Figure 1A:
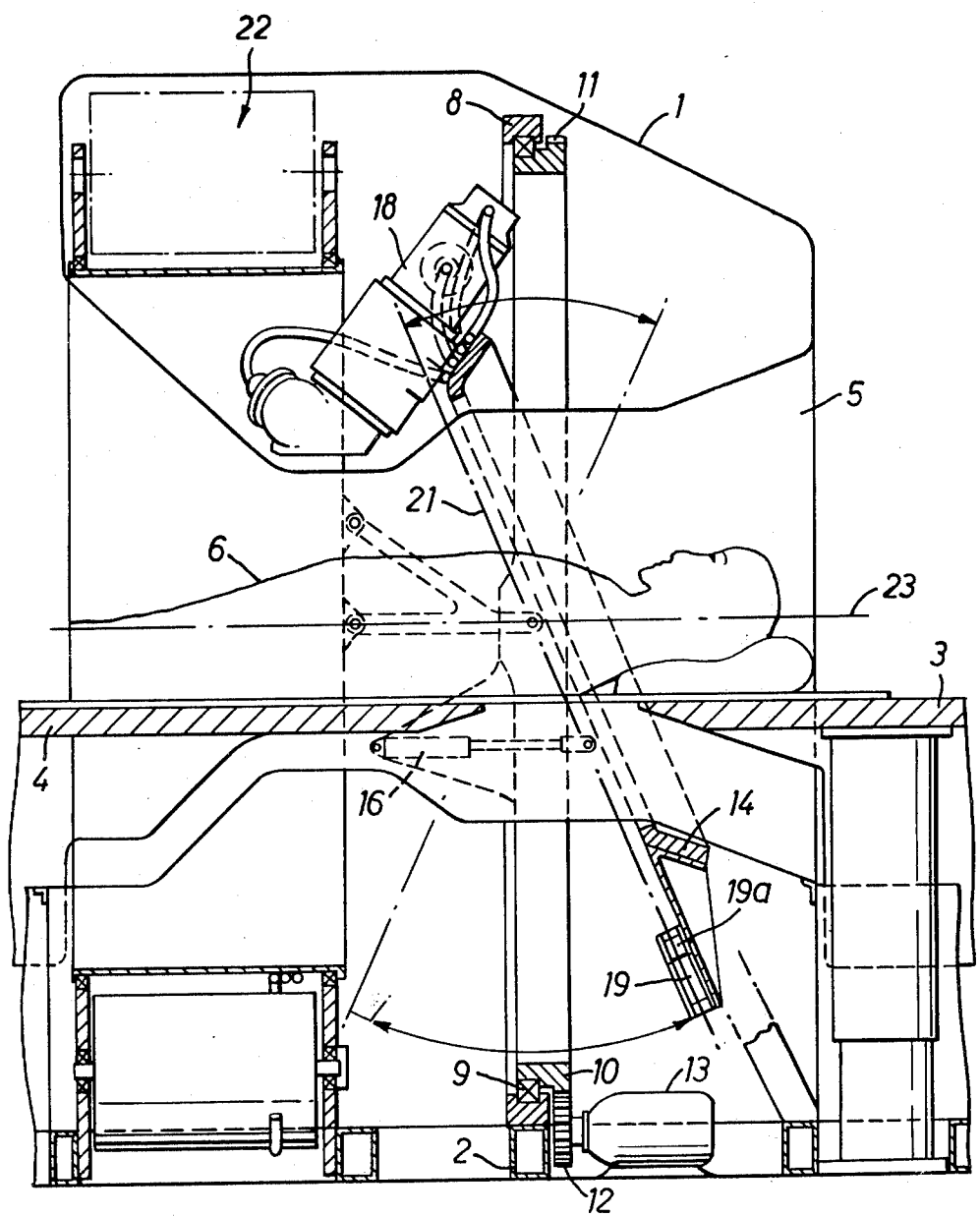

United States Patent [19]

Hounsfield

[11] 4,177,382
[45] Dec. 4, 1979

[54] RADIOGRAPHY

[75] Inventor: Godfrey N. Hounsfield, Newark, England

[73] Assignee: E M I Limited, Hayes, England

[21] Appl. No.: 948,301

[22] Filed: Oct. 3, 1978

Related U.S. Application Data

[63] Continuation of Ser. No. 790,474, Apr. 25, 1977, abandoned.

[30] Foreign Application Priority Data

Apr. 28, 1976 [GB] United Kingdom ............... 17204/76

[51] Int. Cl.² .......................................... G03B 41/16
[52] U.S. Cl. ................................. 250/445 T; 250/360
[58] Field of Search .................. 250/445 T, 523, 360, 250/366

[56] References Cited

U.S. PATENT DOCUMENTS

| 3,922,552 | 11/1975 | Ledley | 250/445 T |
| 3,946,234 | 3/1976 | Hounsfield | 250/445 T |

*Primary Examiner*—Craig E. Church
*Attorney, Agent, or Firm*—Cooper, Dunham, Clark, Griffin & Moran

[57] ABSTRACT

In a computerized tomographic apparatus for medical radiographic purposes, high definition information is sometimes required in respect of a region inside the body. It is therefore necessary to subject that region to a considerable radiation dosage. This gives rise to difficulties of excessive dosage to the skin and other portions of the body surrounding said region. The invention provides an arrangement whereby radiation is projected through said region by way of different areas of the skin so as to provide the high definition information required for said region without subjecting the skin to excessive radiation dosage.

9 Claims, 4 Drawing Figures

RADIOGRAPHY

This is a continuation of application Ser. No. 790,474 filed Apr. 25, 1977 now abandoned.

The present invention relates to radiography, and it relates especially to that branch of radiography which has become known as computerised axial tomography. Apparatus for performing computerised axial tomography is described and claimed in U.S. Pat. No. 3,778,614.

In essence, computerised axial tomography is performed by measuring the absorption suffered by X-radiation on traversing each of many substantially coplanar, pencil-like beam paths through a body and processing signals indicative of the various absorption values to evaluate the absorption coefficient, with respect to the radiation used, at each of a number of locations distributed over the irradiated plane of the body. The processing is preferably effected without transforming the absorption values out of the spatial domain, and suitable processing techniques are described in the aforementioned United States patent and in the specification of U.S. Pat. No. 3,924,129. A visual representation of the evaluated coefficients is provided in any convenient manner.

In some circumstances, it is preferable to evaluate the absorption coefficients with high accuracy only for locations distributed over a particular region of interest in the body, instead of evaluating the coefficients over an entire irradiated plane. This is particularly the case when the absorption coefficients have already been evaluated for locations distributed over an irradiated plane and examination of the corresponding visual representation indicates that an anomaly exists at a certain region of the plane. It is then desirable to obtain more detailed information about the certain region, and possibly also its immediate surroundings. This could be effected by further irradiating the region, either by a single examination with an increased radiation dosage or by effecting a number of examinations, each of relatively low dosage, and combining the information derived from all the examinations. These techniques, however, if effected in the originally irradiated plane of the body, are subject to a serious difficulty, namely that because the region of interest will, in almost all cases be disposed entirely within the body, and because of the attenuation of the radiation by the body tissue and other matter, such as bones, disposed outside the region of interest but in the irradiated plane, the radiation dosage through the region of interest which is necessary to provide the required accuracy of information for said region requires that the patent's skin be subjected to unacceptably high radiation dosages.

It is an object of this invention to provide the facility for obtaining accurate information about a selected region of the body without subjecting the patient's skin to unacceptably high radiation dosage.

According to the invention from one aspect there is provided medical radiographic apparatus comprising means for defining a patient position, generating means for generating a substantially planar, fan shaped distribution of X-radiation, means for mounting said generating means so that said radiation propagates through said patient position, detector means including an array of detector devices disposed in an array extending across said distribution, for detecting radiation projected through said patient position along a plurality of divergent beam paths in said distribution, rotating means causing said generating means and said detector means to rotate around said patient position about a common axis so that said generating means projects said radiation through said patient position from a plurality of locations which conform to a locus disposed in a substantially planar region intersected substantially normally by said axis and so that said detector means detects radiation emergent from the patient position along further groups of beam paths originating from respective ones of said locations, the detector means rotating in a further substantially planar region, spaced from said first-mentioned region and intersected substantially normally by said axis.

According to the invention from another aspect, there is provided radiographic apparatus including a source of X-radiation and detector means responsive to the radiation, the source and the detector means being supported by a scanning mechanism which is formed with an opening to accommodate a patient's body, and the source and the detector means being disposed at opposite sides of the opening so as to respectively project radiation across, and receive radiation projected across, the opening; the scanning mechanism including means for rotating the source and the detector means around the body through more than one revolution, and means for altering the attitudes of the source and the detector means relative to the body so that the radiation is directed through a common region of interest in said body, during successive of said revolutions, by way of different regions of the patient's skin.

Figure 1B:
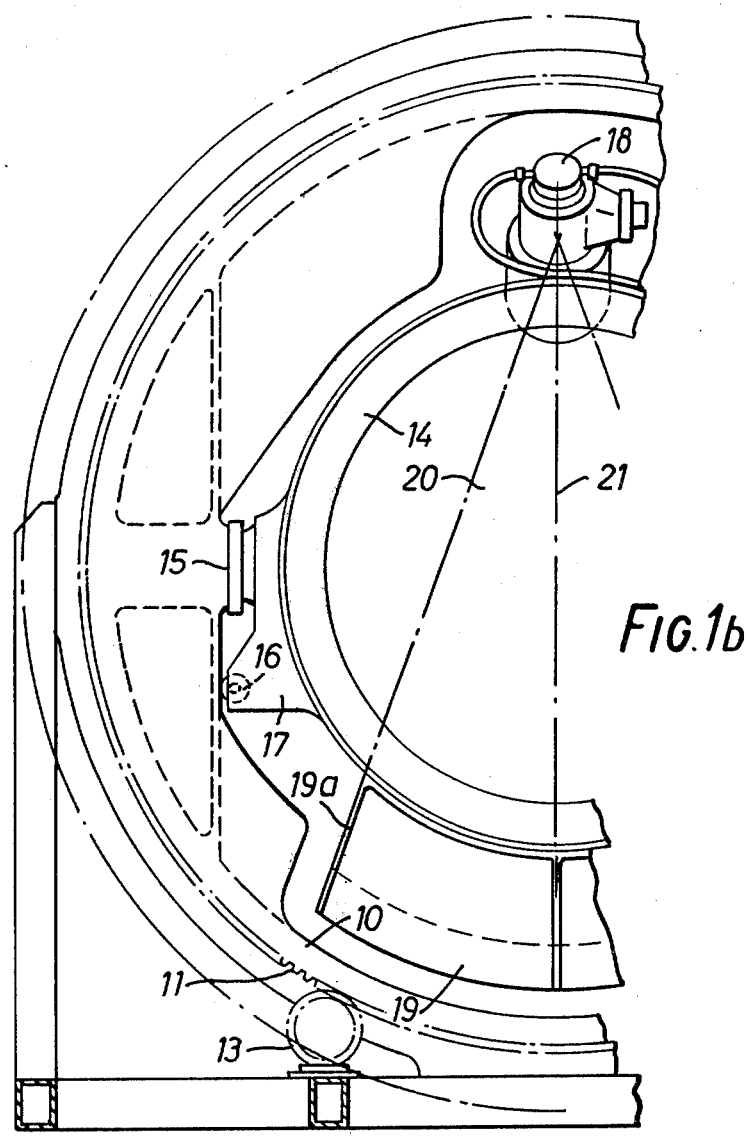
Figure 2:
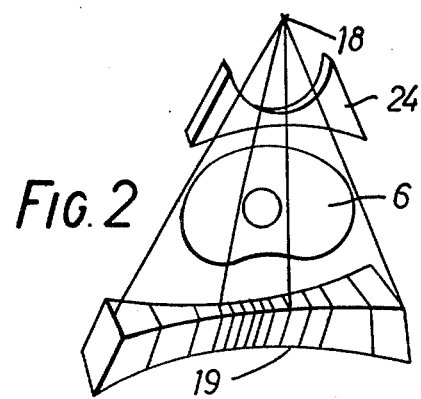

In order that the invention may be clearly understood and readily carried into effect, an embodiment thereof will now be described, by way of example only, with reference to the accompanying drawings of which:

FIG. 1(a) shows, in schematic, cross-sectional view, radiological apparatus in accordance with one example of the invention, FIG. 1(b) shows a view taken on arrows B—B of FIG. 1(a), and FIG. 2 shows, in perspective view, a typical arrangement of detectors and an attenuator.

Referring now to FIGS. 1(a) and 1(b), a radiographic apparatus in accordance with one example of this invention comprises a main housing 1 which has a base 2 secured to the floor and which supports a two-part table 3, 4 which also is static. The main housing 1 is formed with an opening 5 to accommodate the body 6 of a patient to be examined; the body 6 being supported on a platter 7 which is slidably movable relative to the table 3, 4 so that the patient can be moved through the opening 5 to position the body 6 appropriately for the examination.

The body 6 is strapped to the platter by means of a strap (not shown) of plastics material, the strap being preferably transparent to light, as well as to X-radiation, so that a mark on the body 6 which indicates where the examination is to be made can be seen through the strap. This permits the body to be positioned properly by alignment of the mark with a finely focussed beam of light generated by a lamp (not shown) fixed to the main housing 1.

Fixedly mounted within the housing 1 is a main bearing support ring 8 which supports a main bearing 9 in which runs a circular frame 10. Frame 10 is formed with gear teeth 11 which co-operate with gear teeth 12 on a gear wheel driven by an electric motor 13. Mounted in the frame 10 so as to rotate therewith is a sub-frame 14. The sub-frame 14 is pivottably mounted to the frame 10 at two diametrically opposite locations such as 15 in FIG. 1(a), and the angle of tilt of the sub-frame 14 relative to the frame 10 is controlled by a pair of actuators 16, only one of which can be seen in the drawing, which rotates with the frame 10 and urges against respective flanges such as 17 attached to the sub-frame 14.

The sub-frame 14 supports an X-ray source 18 and an array 19 of collimated radiation sensitive detectors such as sodium iodide scintillator crystals with associated photo-diodes or photo-multipliers. The collimators are shown at 19a. The array 19 typically contains a hundred or more detectors.

The source 18 comprises an X-ray tube which emits a fan-like spread of radiation indicated at 20 in FIG. 1(b); the centre line of the fan being shown at 21. The source 18 is preferably of the kind described in U.S. patent applications Ser. Nos. 630,779 (now U.S. Pat. No. 4,010,370) and 733,941 filed Oct. 19, 1976, i.e. in which the electron beam thereof can be scanned over the X-ray producing target thereof to shift the fan of radiation, relative to the body, in a lateral direction. This not necessarily the case, however. If a scanned source is used, however, the line 21 represents the position occupied by the central beam of the fan when the electron beam position is half-way across the target.

Clearly the source has to be supplied with electrical power and with coolant for the target thereof, and the necessary cable connections are allowed for by means of a suitable cable handling system as indicated generally at 22 in FIG. 1(a). Typically such a system is required to accommodate sufficient cable to allow the source 18 to execute five or six revolutions about the body without stopping.

The apparatus can operate with the sub-frame 14 disposed so that the fan 20 is in a vertical plane, the motor 18 being actuated to cause the source 18 and the detector array 19 to orbit around the body with the fan 20 remaining in a vertical plane, about an axis 23 which is horizontal and intersects the body longitudinally thereof; that is the axis of frame 10. The scanning motion of the frame 10 and its attachments and the deflection of the electron beam of the X-ray source 18 are synchronised as described in either of the aforementioned U.S. patent application Ser. Nos. 630,779 and 733,941 and the data so acquired are processed in the manner described in the appropriate one of the two specifications to evaluate the absorption coefficient at each of a plurality of locations distributed over the irradiated plane of the body. The apparatus when so operated effects a similar scanning movement to that described in the aforementioned patent application.

Assuming however, that a visual representation of the evaluated coefficients in a planar section of the body indicates a particular region in the interior of the body 6 which is deemed worthy of further investigation, the present invention is invoked to provide more detailed information about that region. The height and lateral position of the body 6 within the opening 5 is adjusted so as to place the region of particular interest as close as possible to the junction of axis 23 and the line between the mountings 15.

The actuators 16 are then operated so as to tilt the sub-frame 14 by a predetermined angle within the frame 10. The angle of tilt used depends on a number of factors such as the operating conditions of the X-ray source 11 and the resolution with which it is required to investigate the region of interest. The angle of tilt may in some circumstances be as much as 40°, although this would not be possible with the dimensions shown in the drawing, where a tilt of about 25° can be accommodated.

With the angle of tilt having been selected by suitable operation of the actuators 16, the motor 13 is energised to cause the frame 10, and thus the sub-frame 14 and its attachments, to rotate around the body. Because of the tilt introduced by the actuator 16, the source 18 and the detector array 19 rotate in respective vertical planes, the radiation being projected through the body along a figure of revolution which resembles an hour-glass; the waist of the hour-glass being arranged to coincide with the aforementioned region of interest within the patient's body. By adjusting the angle of tilt between successive revolutions of the frame 10, by means of the actuators 16, the radiation can be projected through the body along successive figures of revolution, all of which resemble hour-glasses with their waists being coincident, but the figures of revolution being of varying dimensions in the direction parallel to the actuator movement. Thus, effectively, as the angle of tilt decreases, the planes of rotation of the source 18 and of the detector array 19 become closer together. In the limit, i.e. when the sub-frame 14 is disposed vertically within the frame 10, the figure of revolution is a single plane, which can be regarded as a completely flat hourglass; the plane intersecting the waists of the previously irradiated figures of revolution.

In practice, it is more convenient to cause the actuators 16 to vary the angle of tilt of the sub-frame 14 relative to the frame 10 gradually and smoothly rather than step-wise between successive revolutions as suggested above. This introduces a slight distortion into the irradiated figures of revolution but the distortion is not significant as it occurs mainly in the peripheral regions of the body, away from the region of interest.

Again, in practice, it is usual to cause the apparatus to rotate a number of times, say ten or twelve, about the patient whilst the patient remains in a fixed position, half of the revolutions being in one direction and half in the other. In either case, the first revolution in one direction is used to accelerate the apparatus to its desired operational speed and the last revolution in that direction is used for deceleration; the intermediate revolutions in that direction (i.e. three or four as the case may be) being used for irradiating the body. It is desirable (though not absolutely necessary) for the irradiation to be effected symmetrically about the single vertical plane which is irradiated with the sub-frame 14 vertical. Thus it is preferable to commence with an angle of tilt of $+\alpha°$ and, after the appropriate number of active revolutions, to end with an angle of tilt of $-\alpha°$, the sub-frame 14 having passed through the vertical position exactly half-way through the scanning sequence.

There would be little significance in attempting to use the absorption readings obtained from the detector array 19 during a single revolution of the frame 10 to evaluate the absorption coefficients of elements of the body disposed on the figure of revolution irradiated during that revolution, although this could be done if desired. It is preferable, however, to combine the absorption values derived at the same angular position of the frame 10 for each of the active revolutions thereof around the body, so as to synthesise data relating to waisted beam paths which are relatively broad in passing through peripheral regions of the body but narrow in passing through the aforementioned region of interest. These combined values (one for each detector at each of a large number, say five hundred, of angular positions of the frame 10 around the body) are processed, for example as described in U.S. Pat. No. 3,924,129 as if they were absorption readings relating to a single plane. In practice, of course, the combined absorption readings relate to a concave lens-shaped region of the body; the thinnest part of the lens coinciding with the region of interest in the body.

The use of combined data as described above has advantages in regard to signal-to-noise ratio and also gives enables the region of interest to be investigated with higher accuracy than the surrounding, peripheral regions of the body. This enables the absorption coefficients evaluated for said region of interest to be displayed on an enlarged scale (blown up in photographic parlance) if desired.

This advantageously increased accuracy of evaluation and higher resolution in the region of interest is achieved because that region is irradiated a number of times. A corresponding increase in dosage to a particular region of the skin is avoided however, by means of the invention, because the tilting action of the sub-frame 14 ensures that the radiation enters the body through different areas of skin during different revolutions of the scanning frame 10.

As an extra facility, which is available because of the provision of the tilting sub-frame 14, the actuators 16 can be caused to operate sinusoidally so that the source 18 and the detector array 19 can rotate around the body in a common plane which is tilted with respect to the vertical plane which would be irradiated with the sub-frame 14 vertical. All such tilted planes will, of course, intersect the region of interest of the body provided that this is located at the junction of the axis of rotation 23 of the frame 10 and the axis of tilt. The sinusoidal movement of the actuators 16 is synchronous with the rotation of frame 10, so that precisely one cycle of the sinusoidal motion occurs during one revolution of the frame 10. The angle of tilt relative to the aforementioned vertical plane is determined by the amplitude of the sinusoidal motion, whereas the attitude of tilted plane is determined by the phase of the sinusoidal motion relative to the rotation of frame 10.

It will be appreciated that a display of the absorption coefficients disposed on an inclined plane in the body can be useful in determining the extent and/or shape of an anomaly discovered in an examination of a corresponding display for a vertical plane.

As the detectors towards the extremities of the array 19 are not required to provide highly defined information, they can be made larger than the detectors in the centre of the array, with corresponding reduction in associated circuits and equipment. This broad principle is disclosed in U.S. Pat. No. 3,973,128 which describes and claims an arrangement in which the spacing and/or size of detectors increases towards the extremities of an array adapted to receive radiation projected along a fan-shaped beam. In the present case, the detectors are also made larger in the direction perpendicular to the fan, as shown in highly schematic form in FIG. 2 to fit the hour-glass shape of the cross section irradiated. The outer detectors of the array 19 thus have a large collecting surface for X-rays from the source 18 and accordingly it is possible to attenuate the X-radiation at the edges of the fan quite considerably (e.g. by a factor of 100) as compared with the attenuation of X-radiation in the centre of the fan by means of an attenuator 24 of the kind shown in FIG. 2; this attenuator being interposed between the source 18 and the patient's body to further reduce the dosage of radiation to the patient's skin.

In order to reduce the extent of the housing 1, to reduce the risk of causing concern to patients having claustraphobic tendencies, whilst still permitting the required amount of tilt of the sub-frame 14 relative to the frame 10, it can be advantageous to turn the X-ray tube 18 through 90° so that the aspect presented by the X-ray tube in the view of FIG. 1(a) would be similar to that presented in the view of FIG. 1(b), except that it would probably be turned through 180° with respect to the position shown in FIG. 1(b). This would mean that the thinnest profile of the tube would lie in the direction of tilt.

As described hitherto, the array 12 has comprises a single array of detectors, but if the source 11 is arranged to produce a square, pyramidal shaped beam of radiation then several arrays of such detectors could be used, so as to enable a number of angled planes to be irradiated at one and the same time.

In the event that the region of particular interest in the body in closely adjacent the skin (for example if the spine is to be studied), it can be advantageous to cause the unit 10 and its attachments to only usefully rotate through say 180° or more in each plane, by turning off the X-ray tube during part of the rotation. The arrangement is made such that the radiation never enters the body through the back of the patient in the region of the spine. This reduces radiation dosage to the skin behind the spine.

Figure 3:
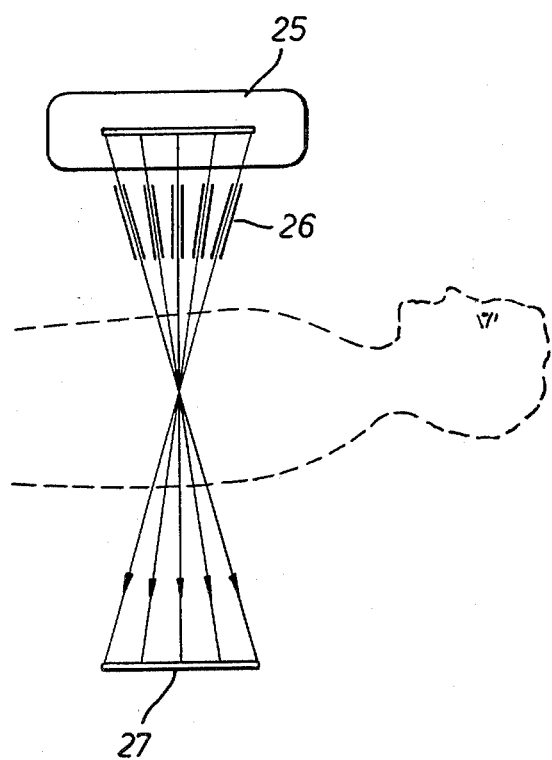

In another embodiment of the invention, as shown in schematic side elevation in FIG. 3, the use of the tilting sub-frame 14 (FIG. 1a) and the necessity for the source and detectors to perform multiple rotations about the patient, are avoided by using instead of the X-ray tube 18 (FIG. 1a) an X-ray tube 25 having a long line focus, say eighteen inches long, measured in a direction parallel to the axis 23 (FIG. 1a). Suitable collimators are used, as indicated at 26, to focus the X-rays from the tube 25 at the centre of the patient's body. The detectors 27 would comprise, say, 400 detector elements, each eighteen inches long to allow for the divergence of the X-rays after they have traversed the centre of the body. It will be understood that the source tube 25 produces a fan-shaped swath of radiation, extending into and out of the plane of FIG. 3, at each point along the anode thereof. The detectors 27 accordingly extend above and below the plane of the Figure. As a compromise between the arrangement just described and that described with respect to FIG. 1, the source 25 could be such as to have an elongated anode of the kind shown in FIG. 3 but, instead of this anode representing a line focus which simultaneously produces several fan-shaped swaths of the radiation, the electron beam of the X-ray tube is focused at a single point of the anode and the beam can be deflected so that said point moves along the anode. This technique would avoid the need for the tilting sub-frame 14 required with the FIG. 1 arrangement but would require that the source and detectors execute multiple rotations around the patient as the deflection would be such as to hold the said point in one position on said anode for one revolution, to shift said point for the next revolution and so-on. A fixed bank of source collimators such as those shown in FIG. 3 would be used.

An alternative technique for achieving the aim of the invention is to demount the main housing 1 from the bed 3, 4 and to rigidly fix the frame 10 relative to said housing. The entire main housing and contents can then be mounted on vertical and horizontal gimbals which can be driven by suitable actuators to effect the required angle or angles of tilt.

What I claim is:

1. Medical radiographic apparatus comprising means for defining a patient position, generating means for generating a substantially planar, fan-shaped distribution of X-radiation, means for mounting said generating means so that said radiation propagates through said patient position, detector means, including an array of detector devices disposed in an array extending across said distribution, for detecting radiation projected through said patient along a plurality of divergent beam paths in said distribution, rotating means causing said generating means and said detector means to rotate around said patient position about respective centers of rotation which are on a common axis so that said generating means projects said radiation through said patient position from a plurality of locations while rotating about its center of rotation and so that said detector means detects radiation emergent from the patient position along further groups of beam paths originating from respective ones of said locations while the detector means rotates about its center of rotation; means being provided to change the spacing between the respective centers of rotation of the generating means and the detector means, such means being synchronised in operation with said rotating means and causing said spacing to change during a number of rotations of said generating means and said detector means around said patient position; the radiation, during all of said rotations, traversing a common region in the vicinity of said axis.

2. Medical radiographic apparatus comprising means for defining a patient position, generating means for generating a substantially planar, fan-shaped distribution of X-radiation, means for mounting said generating means so that said radiation propagates through said patient position, detector means, including an array of detector devices disposed in an array extending across said distribution, for detecting radiation projected through said patient along a plurality of divergent beam paths in said distribution, rotating means causing said generating means and said detector means to rotate around said patient position about a common axis so that said generating means projects said radiation through said patient position from a plurality of locations which conform to a locus disposed in a substantially planar region intersected substantially normally by said axis and so that said detector means detects radiation emergent from the patient position along further groups of beam paths originating from respective ones of said locations, the detector means rotating in a further substantially planar region, spaced from said first-mentioned region and intersected substantially normally by said axis; wherein said rotating means comprises a main frame having an aperture of sufficient size to accommodate said patient position, means for rotating said main frame about said axis, said axis passing through said aperture, a sub-frame having an aperture of sufficient size to accommodate said patient position, means mounting said generating means and said detector means to said sub-frame and tilt means for controllably tilting said sub-frame, relative to said main frame, in a direction substantially parallel to said axis.

3. Apparatus according to claim 2 including two pivotal mounts, disposed at diametrically opposite locations of said main frame, by means of which said sub-frame is pivotably mounted to said main frame.

4. Apparatus according to claim 2 wherein said tilt means includes a pair of actuators.

5. Apparatus according to claim 2 wherein, in operation, the angle of tilt of said sub-frame relative to said main frame is held substantially constant for a first revolution of said main frame about said axis and is changed for the next and subsequent revolutions.

6. Apparatus according to claim 2 wherein, in operation, the angle of tilt of said sub-frame relative to said main frame is changed gradually during revolution of said main frame about said axis.

7. Apparatus according to claim 2 wherein said generating means includes an X-ray tube having an X-ray emissive anode which is elongated in a direction substantially parallel to said axis and collimator means for selecting, from the X-radiaiton emitted by said elongated anode, a plurality of mutually inclined, substantially planar, fan-shaped distributions of X-radiation each directed towards a respective detector means.

8. Apparatus according to claim 7 wherein said distributions are generated simultaneously.

9. Apparatus according to claim 7 wherein said distributions are generated sequentially, one for each of a number of successive revolutions of said main frame about said axis.

* * * * *